United States Patent
Weissman et al.

(12) 
(10) Patent No.: US 6,395,887 B1
(45) Date of Patent: *May 28, 2002

(54) ANALYSIS OF GENE EXPRESSION BY DISPLAY OF 3'-END FRAGMENTS OF CDNAS

(75) Inventors: Sherman M. Weissman, New Haven, CT (US); Yatindra Prashar, Columbia, MD (US)

(73) Assignee: Yale University, New Haven, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 8 days.

This patent is subject to a terminal disclaimer.

(21) Appl. No.: 08/970,166

(22) Filed: Nov. 12, 1997

Related U.S. Application Data

(63) Continuation-in-part of application No. 08/688,514, filed on Jul. 30, 1996, now Pat. No. 6,010,850, and a continuation-in-part of application No. 08/946,227, filed on Oct. 7, 1997, now abandoned, which is a continuation-in-part of application No. 08/510,032, filed on Aug. 1, 1995, now Pat. No. 5,712,126.

(51) Int. Cl.[7] ............... C12P 19/34; C07H 19/00; C07H 21/04; C07H 21/00

(52) U.S. Cl. ............... 536/23.1; 435/91.2; 435/91.52; 536/22.1; 536/24.2; 536/24.3; 536/25.3

(58) Field of Search ............... 435/91.2, 91.52; 536/27.1, 24.2, 24.3, 25.3

(56) References Cited

U.S. PATENT DOCUMENTS

| | | | |
|---|---|---|---|
| 5,262,311 A | 11/1993 | Pardee et al. | 435/91.2 |
| 5,459,037 A | 10/1995 | Sutcliffe et al. | 435/6 |
| 5,712,126 A | 1/1998 | Weissman et al. | 435/91.2 |

FOREIGN PATENT DOCUMENTS

| | | | |
|---|---|---|---|
| EP | 0534858 | 3/1993 | C12Q/1/68 |

OTHER PUBLICATIONS

Cecchini et al. (1993) Nucleic Acids Research 21:5742–7.
Chenchik et al. (1996) BioTechniques 21:526–534.
Diachenko et al. (1996) Biochem. and Biophys.Res. Commun. 219:824–828.
Duguid et al. (1990) Nucleic Acids Research 9:2789–92.
Fischer et al., "Restriction fragment length polymorphism–coupled domain–directed differential display: A highly efficient technique for expression analysis of multigene families," Proc. Natl. Acad. Sci. USA 92:5331–5335, 1995.
Frohman et al., "Rapid production of full–length cDNAs from rare transcripts: Amplification using a single gene–specific oligonucleotide primer," Proc. Natl. Acad. Sci. USA 85:8998–9002, 1988.
Kato (1996) Nucleic Acids Res. 24:394–395.
Kato (1995) Nucleic Acids Res. 23:3685–3690.
Ko et al., "Unbiased amplification of a highly complex mixture of DNA fragments by 'lone linker'— tagged PCR," Nucleic Acids Research 18(14):4293, 1990.

(List continued on next page.)

*Primary Examiner*—Kenneth R. Horlick
*Assistant Examiner*—J. Tung
(74) *Attorney, Agent, or Firm*—Morgan, Lewis & Bockius LLP

(57) ABSTRACT

The present invention is directed to an approach to identify changes in gene expression by selective amplification of 3' fragments of double stranded cDNAs.

63 Claims, 9 Drawing Sheets

OTHER PUBLICATIONS

Liang et al. (1994) Nucleic Acids Research 22:5763–4.

Lisitsyn et al. (1993) Science 259:946–951.

Loh et al., "Polymerase Chain Reaction with Single–Sided Specificity: Analysis of T Cell Receptor δ Chain," Science 243:217–220, 1989.

Navarro et al. (1996) J. Virol. Methods 56:59–66.

Prashar et al., "Analysis of differential gene expression by display of 3' end restriction fragments of cDNAs," Proc. Natl. Acad. Sci USA 93:659–663, 1996.

Roux et al., "A Strategy for Single site PCR Amplification of dsDNA: Priming Digested Cloned or Genomic DNA from an Anchor–Modified Restriction Site and a Short Internal Sequence," BioTechniques 8(1):48, 1990.

Straus et al., "Genomic subtraction for cloning DNA corresponding to deletion mutations," Proc. Natl. Acad. Sci. USA, 87:1889–1893, 1990.

Wang et al., (1991) Proc. Natl. Acad. Sci. USA 88.11505–9.

Zhao et al., "New Primer Strategy Improves Precision of Differential Display," BioTechniques 18(5):842–850, 1995.

Liang et al., Differential Display and Cloning of Messenger RNAs from Human Breast Cancer versus Mammary Epithelial Cells,: Cancer Reserch 52:6966–6968, 1992.

Liang et al., "Distribution and cloning of eukaryotic mRNAs by means of differential display: refinements and optimization," Nucleic Acids Research 21(14):3269–3275, 1993.

Reeves et al., "General Method for PCR Amplification and Direct Sequencing of mRNA Differential Display Products," BioTechniques 18(1):18–20, 1995.

Zeng et al., (1994) Nucleic Acids Research 22:4381–5.

Liang et al., "Differential Display of Eukaryotic Messenger RNA by Means of the Polymerase Chain Reaction," Science 257:967–971, 1992.

Averboukh et al., "Better Gel Resolution and Longer cDNAs Increase the Precision of Differential Display," BioTechniques 20(5):918–921, 1996.

Oefner et al., "High–performance Liquid Chromatography for Routine Analysis of Hepatitis C Virus cDNA/PCR products," BioTechniques 16(5):898–908, 1994.

Sargent et al., "Differential Gene Expression in the Gastrula of *Xenopus laevis*," Science 222:135–139, 1983.

St. John et al., "Isolation of Galactose–Inducible DNA Sequences from *Saccharomyces cerevisiae* by Differential Plaque Filter Hybridization," Cell 16:443–452, 1979.

1st STRAND cDNA SYNTHESIS USING PRIMERS $(dT)_n$ - dA $(dT)_n$ - dC $(dT)_n$ - dG

↓

DOUBLE STRAND cDNA SYNTHESIS

↓

RESTRICTION DIGEST

↓

LIGATE ADAPTER

↓

AMPLIFY IN 12 REACTIONS USING PRIMERS:

$(dT)_n$ - dA $\begin{pmatrix} dA \\ dC \\ dG \\ dT \end{pmatrix}$ $(dT)_n$ - dC $\begin{pmatrix} dA \\ dC \\ dG \\ dT \end{pmatrix}$   +    FROM ADAPTER $(dT)_n$ - dG $\begin{pmatrix} dA \\ dC \\ dG \\ dT \end{pmatrix}$

| | | | | | |
|---|---|---|---|---|---|
| 1 |  | TA1 | 8 |  | JkA6 |
| 2 |  | JkA1 | 9 |  | JkA7 |
| 3 |  | JkA2 | 10 |  | JkA8 |
| 4 |  | JkA3 | 11 |  | JkA9 |
| 5 |  | JkA4 | 12 |  | JkA10 |
| 6 |  | JkA5 | 13 |  | JkA11 |
| 7 |  | JkR1 | 14 |  | IL-2 |
| 7(a) |  | | 15 |  | β-Actin |

Changes in Gene Expression in Aging IMR.90 Cells

ANALYSIS OF GENE EXPRESSION BY DISPLAY OF 3'-END FRAGMENTS OF CDNAS

CROSS-REFERENCE TO RELATED APPLICATION

The application is a continuation-in-part of U.S. application Ser. No. 08/688,514. filed Jul. 30, 1996, now U.S. Pat. No. 6,010,850 and U.S. application Ser. No. 08/946,227, filed Oct. 7, 1997, now abandoned which are continuations-in-part of U.S. application Ser. No. 08/510,032, now U.S. Pat. No. 5,712,126 filed Aug. 1, 1995.

STATEMENT OF GOVERNMENT INTEREST

This invention was made, at least in part, with government support under grant number CA-42556-10, awarded by the Department of Health and Human Services. As such, the government may have certain rights in the invention.

TECHNICAL FIELD OF THE INVENTION

This invention generally provides methods for determining a signature profile of mRNAs expressed in a cell.

BACKGROUND OF THE INVENTION

Each cell from a larger eukaryote expresses approximately 15,000 genes. Of these. as few as one gene may account for a particular phenotype. The identification of those genes associated with development, differentiation, disease states, and response to cellular environment is crucial for understanding of these phenomena. A powerful approach to analyze genes responsible for various cell states is to identify genes that are expressed at higher or lower levels in one cell as compared to a reference cell. Specifically, effective and efficient methods are needed to identify and isolate those genes that are differentially expressed in various cells or under altered cell environments.

Early methods developed to identify and clone such genes were primarily based on the principle of differential or subtractive hybridization (see St. John and Davis, *Cell* 16:443, 1979; Sargent and Dawid, *Science* 222:135, 1983). Despite the usefulness of these methods, several limitations restrict their widespread utility: only a fraction of the overall changes in gene expression are measured, large amounts of ribonucleic acid (RNA) are necessary, and the procedures are complex and labor intensive.

Recent development of an amplification technique, called differential display, allows a more comprehensive analysis of messenger RNAs (mRNAs) (Liang and Pardee, *Science* 257:967, 1992; U.S. Pat. No. 5,262,311). The general strategy is to amplify partial cDNA sequences derived from subsets of mRNAs by reverse transcription and polymerase chain reaction. These partial sequences are generated by using a primer that anneals to the 3' end of all mRNAs and a short, random sequence primer that anneals to a subset (approximately 50–100) of mRNAs. The amplified products are then separated by gel electrophoresis and visualized. Although this method yields patterns of mRNAs, documented artifacts render interpretation of the results difficult. Such artifacts stem from the use of random sequence primers, which must be annealed at non-stringent conditions. In addition, the cell source of the mRNAs may be relatively scarce. For example, stem cell populations constitute a very small fraction of a tissue. The amount of RNA recovered from a small number of cells may be too low to allow multiple reactions, which are necessary for generating a profile. In such cases, differential display methods, including that described in '311 patent and in Prashar and Weissman, *Proc. Natl. Acad. Sci. USA* 93:659, 1996, are difficult to perform.

Thus, there is a need in the art for methods of differential display that bypass such artifactual pitfalls and can be readily performed with small amounts of RNA. The present invention provides such an improved method of differential display as well as other related advantages.

SUMMARY OF THE INVENTION

The present invention generally provides methods for selectively amplifying DNA fragments from nucleic acid samples with sequences corresponding to 3' ends of mRNAs.

In one aspect, the invention provides such a method comprising the steps of: (a) contacting the mRNAs with oligonucleotide primers comprising a 5' sequence incapable of hybridizing to a polyA tail of the mRNAs, and a 3' sequence that hybridizes to a portion of the polyA tail of the mRNAs and n non-polyA nucleotides immediately upstream of the polyA tail, wherein n is at least one; (b) reverse transcribing the mRNA to produce a first strand cDNA complementary to the mRNA that includes the oligonucleotide primer; (c) synthesizing a second DNA strand complementary to the first strand cDNA to form a duplex; (d) cleaving the duplex with at least one sequence-specific cleaving agent to provide a number of duplex cleavage fragments; (e) ligating an adapter to the cleavage fragments, the adapter consisting of two partially hybridized nucleic acid strands, wherein portions of the two strands are non-complementary to each other and portions of the two strands are complementary to each other; and (f) amplifying the ligated cleaved fragments using a set of primers, in which for each set the first primer comprises the 5' sequence incapable of hybridizing to a polyA tail of the mRNAs, and the 3' sequence that hybridizes to a portion of the polyA tail of the mRNAs and at least n+1 non-polyA nucleotides immediately upstream of the polyA tail, and a second primer whose sequence comprises at least a portion of the sequence of one strand of the adapter in the non-complementary portion, thereby selectively amplifying a DNA fragment comprising sequence complementary to an 3' region of an mRNA.

In a preferred embodiment, each oligonucleotide primer in step (a) has a different 5' sequence. In a related embodiment, the oligonucleotide primer of step (a) has one non-polyA nucleotide (e.g., 5'-A-3', 5'-C-3', 5'-G-3') and the first primer of step (f) has two non-polyA nucleotides (e.g., 5'-AA-3', 5'-AT-3', 5'-AC-3', 5'-AG-3', 5'-CA-3', 5'-CT-3', 5'-CC-3', 5'-CG-3', 5'-GA-3', 5'-GT-3', 5'-GC-3', and 5'-GG-3'). The contacting step of the method may also be performed with a mixture of oligonucleotide primers. The method may also use each set of primers in step (f) are used in a separate amplification. Furthermore, the 5' sequence of one or both of the primer sequences in step (f) may comprise a recognition sequence for a restriction enzyme. In other preferred embodiments, at least one of the primers in step (f) is labeled, such as with a fluorescent label.

In another preferred embodiment, the adapter comprises a first portion, wherein the two strands are noncomplementary to each other and a second portion, wherein the two strands are complementary to each other, resulting in a partially hybridized adapter that is Y-shaped. Moreover, in certain embodiments, one of the two strands of the noncomplementary portion comprises a recognition sequence for a restriction enzyme.

In related aspects, the present invention provides a method for selectively isolating in a nucleic acid sample DNA fragments having sequences corresponding to 3' ends of mRNAs, comprising the steps above plus isolating the amplified fragment; cloning the isolated fragment, such as by digesting the amplified fragments in step (f) with a restriction enzyme, and ligating the digested fragments to a vector, and further determining the DNA sequence of the isolated fragment; isolating and analyzing the amplified fragment (e.g., determining the DNA sequence, hybridizing to nucleic acid molecules); and detecting the amplified fragments (e.g., by hybridizing the fragments to nucleic acid molecules.

In preferred embodiments, the nucleic acid molecules are attached to a silicon wafer or porous glass wafer, the nucleic acid molecules are oligonucleotides from about 25 to about 40 nucleotides long, the nucleic acid molecules comprise a set of cDNA sequences, and/or the fragments are labeled.

In yet another aspect, the invention provides a method for comparing the levels of mRNA expression in two cell populations, comprising: selectively amplifying in a nucleic acid sample from each cell population DNA fragments having sequences corresponding to 3' portions of mRNAs and comparing the amounts of amplified fragments. In preferred embodiments, one of the cell populations is treated or is a tumor cell population.

The invention also provides a method for selectively amplifying in a nucleic acid sample DNA fragments having sequences corresponding to 3' ends of mRNAs, comprising the steps of: (a) contacting the mRNAs with oligonucleotide primers comprising a sequence that hybridizes to a portion of the polyA tail of the mRNAs and n non-polyA nucleotides immediately upstream of the polyA tail, wherein n is at least one; (b) reverse transcribing the mRNA to produce a first strand cDNA complementary to the mRNA that includes the oligonucleotide primer; (c) synthesizing a second DNA strand complementary to the first strand cDNA to form a duplex; (d) cleaving the duplex with at least one sequence-specific cleaving agent to provide a number of duplex cleavage fragments; (e) ligating an adapter to the cleavage fragments, the adapter consisting of two partially hybridized nucleic acid strands, wherein portions of the two strands are non-complementary to each other and portions of the two strands are complementary to each other; and (f) amplifying the ligated cleaved fragments using a set of primers, in which for each set the first primer comprises the sequence that hybridizes to a portion of the polyA tail of the mRNAs and n+1 non-polyA nucleotides immediately upstream of the polyA tail, and a second primer whose sequence comprises at least a portion of the sequence of one strand of the adapter in the non-complementary portion, thereby selectively amplifying a DNA fragment comprising sequence complementary to an 3' region of an mRNA.

These and other aspects of the present invention will become evident upon reference to the following detailed description and attached drawings. In addition, various references are set forth below which describe in more detail certain procedures or compositions (e.g., plasmids, etc.), and are therefore incorporated by reference in their entirety.

DETAILED DESCRIPTION OF THE INVENTION

Prior to setting forth the invention, it will be helpful to an understanding thereof to set forth definitions of certain terms used herein.

Nucleotides, including deoxynucleotides and nucleotide derivatives, are referred to according to standard abbreviations: "A", deoxyadenylate; "C", deoxycytidylate; "G", deoxyguanylate; "T", deoxythymidylate; "U", uridylate; "M", A or C; "R", A or G; "W", A or T; "S", C or G; "Y", C or T; "K", G or T; "V" A, C, or G; "H", A, C or T; "D", A, G, or T; "B", C, G, or T; and "N", A, C, T, or G. Wherever, nucleotides are specified, nucleotide derivatives or infrequently used nucleotides, may be used as long as the function of the molecule is not inhibited. For example, a dideoxynucleotide should not be used at the 3' end of a primer for synthesis.

I. SELECTIVE AMPLIFICATION OF 3' END FRAGMENTS OF mRNAs

As noted above, the present invention provides methods for selectively amplifying DNA fragments that have sequences corresponding to 3' portions of mRNAs isolated from a biological source. As discussed below in more detail, in preferred aspects, cDNA is first synthesized using a set of oligonucleotide primers, in which each primer comprises an optional 5' sequence incapable of hybridizing to a polyA tail of the mRNAs and a 3' sequence that hybridizes to a portion of the polyA tail and n non-polyA nucleotides immediately upstream of the polyA tail, wherein n is at least one. The double-stranded cDNA is then digested in a sequence-specific manner, ligated with a partially-double stranded adapter, and amplified using a set of primers, in which one primer has the same characteristics of the oligonucleotide primer above but that hybridizes to n+1 or more non-polyA nucleotides and a second primer whose sequence comprises at least a portion of the sequence of one strand of the adapter. These amplified fragments may then be analyzed, subjected to DNA sequence analysis, hybridized to sets of nucleic acids (e.g., oligos), and the like.

A. General Protocols for Selective Amplification

Figure 1:
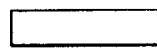
FIG. 1 is an outline schematic of a preferred embodiment of a method for amplification of 3' end fragments of cDNAs.
Figure 1:
Figure 1:
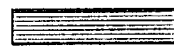
Figure 1:
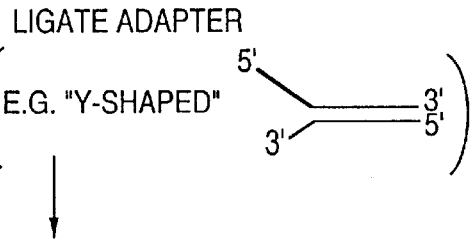
Figure 1:
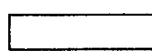
Figure 1:
Figure 1:
Figure 1:

As noted above, the present invention provides methods for selectively amplifying in a nucleic acid sample a DNA fragment having sequences corresponding to 3' portions of mRNAs. Briefly, the method comprises synthesizing double-stranded cDNA in which the reverse transcription of mRNAs uses a set of oligonucleotide primers for first strand synthesis, which does not bind a polyA tail of mRNA, and a 3' sequence that hybridizes to a portion of the polyA tail of the mRNA and at least one non-polyA nucleotide immediately upstream of the polyA tail (an anchored primer). Preferably, although not necessary, each primer pair has a different 5' sequence and 3' sequence in the portion that hybridizes to the non-polyA nucleotide. The duplex is then digested with at least one sequence-specific cleaving agent (e.g., restriction enzyme) to provide a number of cleavage fragments and ligated to a partially double-stranded adapter. These fragments are amplified to produce products corresponding to the 3' end of mRNAs, using a first primer whose sequence comprises the oligonucleotide primer sequence with at least one additional nucleotide at the 3' end and a second primer sequence derived from the adapter (FIG. 1).

In a related aspect, the method selectively amplifies DNA fragments having sequences complementary to 3' portions of mRNAs. Briefly, the method comprises synthesis of double-stranded cDNA, in which the reverse transcriptase primes from a set of oligonucleotide primers each comprising a sequence that hybridizes to a portion of the polyA tail of the mRNA and at least one non-polyA nucleotide immediately upstream of the polyA tail. The double-stranded cDNA is then cleaved with a sequence-specific cleaving agent to provide cleavage fragments. These fragments are ligated to a partially double stranded adapter and amplified with a set of primers consisting of a first primer whose sequence comprises the oligonucleotide primer sequence with an additional nucleotide at the 3' end and a second primer sequence derived from the adapter. Thus, DNA fragments comprising sequence complementary to 3' sequences of mRNAs are amplified.

Amplification may be performed by any of a variety of techniques. Such techniques include, but are not limited to, polymerase chain reaction, isothermal amplification, cycling probe amplification, and the like. Conditions for polymerase chain reaction, the preferred method, are well known.

Should there be multiple fragments having the same or nearly the same length, additional cleavage reactions can be performed to resolve the fragments. The cleavage can be done before or after amplification, and will typically be the result of using a restriction enzyme. Using such an approach to amplify 3' end fragments of cDNA, additional differentially expressed RNAs are observed in activated Jurkat cells as compared to untreated cells. (see, Examples).

B. Components of the Methods

As described above, the method first requires a source of mRNAs, which are isolated from a cell source. The cells may be obtained from an in vivo source, such as a tumor, blood, liver, or other organs, from sources such as soil, food, excrement, and the like, or from in vitro sources, such as tissue culture. As is apparent to one skilled in the art, any cell type may be used. Furthermore, the cells that are initially obtained may be subjected to various separation techniques (e.g., flow cytometry, density gradients), treatments (e.g., contact with drugs, small molecules), and the like. Especially when two cell populations are to be compared, each population may undergo a different treatment or handling.

mRNAs are isolated from cells by any one of a variety of techniques. Numerous techniques are well known (see, e.g., Sambrook et al., *Molecular Cloning: A Laboratory Approach*, Cold Spring Harbor Press, NY, 1987; Ausubel et al., *Current Protocols in Molecular Biology*, Greene Publishing Co. NY, 1995). In general, these techniques first lyse the cells and then enrich for or purify RNA. In one such protocol, cells are lysed in a Tris-buffered solution containing SDS. The lysate is extracted with phenol:chloroform, and nucleic acids precipitated. The mRNAs may be purified from crude preparations of nucleic acids or from total RNA by chromatography, such as binding and elution from oligo (dT)-cellulose or poly(U)-Sepharose®. However, purification of poly(A)-containing RNA is not a requisite. As stated above, other protocols and methods for isolation of RNAs may be substituted.

The mRNAs are reverse transcribed using an RNA-directed DNA polymerase, such as reverse transcriptase isolated from AMV, Mo-MuLV or produced by recombinant means. Many commercial sources of enzyme are available (e.g., Pharmacia, New England Biolabs, Stratagene Cloning Systems). Suitable buffers, cofactors, and conditions are well known and generally supplied by manufacturers (see also Sambrook et al., supra; Ausubel et al., supra).

In the present invention, various oligonucleotides are used. In particular, the methods utilize oligonucleotide primers for cDNA synthesis, adapters, and primers for amplification. Oligonucleotides are generally synthesized as single strands by standard chemistry techniques, including automated synthesis. Oligonucleotides are subsequently de-protected and may be purified by precipitation with ethanol, chromatographed using a sizing or reversed-phase column, denaturing polyacrylamide gel electrophoresis, high-pressure liquid chromatography (HPLC), or other suitable method. In addition, within certain preferred embodiments, a functional group, such as biotin, is incorporated, preferably at the 5' or 3' terminal nucleotide. A biotinylated oligonucleotide may be synthesized using pre-coupled nucleotides, or alternatively, biotin may be conjugated to the oligonucleotide using standard chemical reactions. Other functional groups, such as fluorescent dyes, radioactive molecules, digoxigenin, and the like, may also be incorporated.

Partially-double stranded adapters are formed from single-stranded oligonucleotides by annealing complementary single-stranded oligonucleotides that are chemically synthesized or by enzymatic synthesis. Following synthesis of each strand, the two oligonucleotide strands are mixed together in a buffered salt solution (e.g., 1 M NaCl, 100 mM Tris-HCl pH 8.0, 10 mM EDTA) or in a buffered solution containing $Mg^{2+}$ (e.g., 10 mM $MgCl_2$) and annealed by heating to high temperature and slow cooling to room temperature. Other recognized methods to anneal the adapters may be alternatively used.

In a preferred aspect, the oligonucleotide primers that prime first strand DNA synthesis comprise a 5' sequence incapable of hybridizing to a polyA tail of the mRNAs, and a 3' sequence that hybridizes to a portion of the polyA tail of the mRNAs and at least one non-polyA nucleotide immediately upstream of the polyA tail. In one embodiment, the 5' sequence is the same for each primer; in a related embodiment, the 5' sequence is different for each primer. A schematic of representative primers are shown in FIG. 1. The 5' sequence is preferably a sufficient length that it increases specificity in the amplification step. Although any length will increase specificty, the 5' sequence is preferably at least 12 bases. The 5' sequence also preferably has an average G+C content and does not contain a large palindrome sequence; some palindromes, such as a recognition sequence for a restriction enzyme, may be acceptable. Examples of suitable 5' sequences may be found in Table 1. In certain aspects, the oligonucleotide primer lacks such a 5' sequence.

The 5' sequence, if present, is joined to a 3' sequence comprising sequence that hybridizes to a portion of the polyA tail of mRNAs and at least one non-polyA nucleotide immediately upstream. Although the polyA-hybridizing sequence is typically a homopolymer of dT or dU, it need only contain a sufficient number of dT or dU bases to hybridize to polyA under the conditions employed. Both oligo(dT) and oligo(dU) primers give comparable results. Thus, other bases may be present, interspersed or concentrated, as long as hybridization is not impeded. Typically, 12 to 18 bases or 12 to 30 bases of dT or dU will be used. However, as one skilled in the art appreciates, the length need only be sufficient to obtain hybridization. The non-polyA complementary nucleotide is A, C, or G, or a nucleotide derivative, such as inosinate. If one non-polyA complementary nucleotide is used, then three oligonucleotide primers are needed to hybridize to all mRNAs. If two non-polyA complementary nucleotides are used, then 12 primers are needed to hybridize to all mRNAs (AA, AC, AG, AT, CA, CC, CG, CT, GA, GC, GG, GT). If three non-polyA complementary nucleotides are used then 48 primers are needed (3×4×4). Although there is no theoretical upper limit on the number of non-polyA nucleotides, practical considerations make the use of one or two non-polyA complementary nucleotides preferable, and one non-polyA complementary nucleotide particularly preferred.

For cDNA synthesis, the mRNAs may be subdivided into three fractions (if one non-polyA complementary nucleotide is used) or 12 fractions (if two non-polyA complementary nucleotides are used), each containing a single oligonucleotide primer or, the primers may be pooled and contacted with an undivided mRNA preparation. Other subdivision schemes may alternatively be used. Briefly, first strand cDNA is initiated from the oligonucleotide primer by reverse transcriptase (RTase). As noted above, RTase may be obtained from numerous sources and protocols are well known. Second strand synthesis may be performed by RTase (Gubler and Hoffman, *Gene* 25: 263, 1983), which also has a DNA-directed DNA polymerase activity, with or without a specific primer, by DNA polymerase I in conjunction with RNaseH and DNA ligase, or other equivalent methods. The double-stranded cDNA is generally treated by phenol:chloroform extraction and ethanol precipitation to remove protein and free nucleotides.

Double-stranded cDNA is subsequently digested with an agent that cleaves in a sequence-specific manner. Such cleaving agents include restriction enzymes, chemical agents, triple helix methods, and the like. Restriction enzyme digestion is preferred; enzymes that are relatively infrequent cutters (e.g., ≧5 bp recognition site) are preferred and those that leave overhanging ends are especially preferred. A restriction enzyme with a six base pair recognition site cuts approximately 8% of cDNAs, so that approximately 12 such restriction enzymes should be needed to digest every cDNA at least once. By using 30 restriction enzymes, digestion of every cDNA is essentially assured.

The adapters for use in the present invention are generally designed such that the two strands are only partially complementary and only one of the nucleic acid strands can be amplified. Thus, the adapter is partially double-stranded (i.e., comprising two partially hybridized nucleic acid strands), wherein portions of the two strands are non-complementary to each other and portions of the two strands are complementary to each other. Conceptually, the adapter is "Y-shaped" or "bubble-shaped." When the 5' region is non-paired, the 3' end of the other strand cannot be extended by a polymerase to make a complementary copy. The ligated adapter can also be blocked at the 3' end to eliminate extension during subsequent amplifications. Blocking groups include dideoxynucleotides and the like. In this type of adapter ("Y-shaped"), the non-complementary portion of the upper strand of the adapter is preferably a length that can serve as a primer for amplification. As noted above, the non-complementary portion of the lower strand need only be one base, however, a longer sequence is preferable (e.g., 3 to 20 bases; 3 to 15 bases; 5 to 15 bases). The complementary portion of the adapter should be long enough to form a duplex under conditions of ligation.

For "bubble-shaped" adapters, the non-complementary portion of the upper strands is preferably a length that can serve as a primer for amplification. Thus, this portion is preferably 15–30 bases. Alternatively, the adapter can have a structure similar to the Y-shaped adapter, but has a 3' end that contains a moiety, including a dideoxynucleotide, that a DNA polymerase cannot extend from.

Amplification primers are also used in the present invention. In the amplification step, the 3' end (referenced to mRNA) of double stranded cDNA that has been cleaved and ligated with an adapter is amplified. For this amplification, a primer pair is used. This pair consists of a first primer whose sequence comprises at least a portion of the oligonucleotide primer as described above, but has at least one additional nucleotide at the 3' end that is complementary to the non-polyA portion; and a second primer whose sequence comprises at least a portion of the sequence of one strand of the adapter in the non-complementary portion. For example, if the primer used in cDNA synthesis has one non-polyA complementary nucleotide, the first amplification primer has at least two. As well, when a 5' sequence is present in the primer used in cDNA synthesis, the first amplification primer will comprise at least a portion of that sequence, and preferably all. As will be appreciated in this scheme, for each additional nucleotide, four primers are needed to cover all possible sequences. Thus, if the 3' base of one of the cDNA synthesis primers is A; the 3' bases of the amplification primers are AA, AC, AG, and AT. Examples of primers used for cDNA synthesis and for amplification are presented in Tables 1 and 2 below.

The second amplification primer will generally contain all the sequence of the non-complementary portion, but may contain less of the sequence, especially when the non-complementary portion is very long, or more of the sequence, especially when the non-complementary portion is very short. In some embodiments, the primer will contain sequence of the complementary portion, as long as that sequence does not appreciably hybridize to the other strand of the adapter under the amplification conditions employed. For example, in one embodiment, the primer sequence comprises four bases of the complementary region to yield a 19 base primer, and amplification cycles are performed at 56° C. (annealing temperature), 72° C. (extension temperature), and 94° C. (denaturation temperature). In another embodiment, the primer is 25 bases long and has 10 bases of sequence in the complementary portion. Amplification cycles for this primer are performed at 68° C. (annealing and extension temperature) and 94° C. (denaturation temperature). By using these longer primers, the specificity of priming is increased.

The design of the amplification primers will generally follow well-known guidelines, such as average G+C content, absence of hairpin structures, inability to form primer-dimers and the like. At times however, it will be recognized that deviations from such guidelines may be appropriate or desirable.

II. ANALYSES

A. Size Analysis

In one embodiment of the present invention, the lengths of the amplified 3' fragments are determined. Any procedure that separates nucleic acids on the basis of size and allows detection or identification of the nucleic acids is acceptable. Such procedures include slab gel electrophoresis, capillary gel electrophoresis, high performance liquid chromatography, and the like.

Electrophoresis is technique based on the mobility of DNA in an electric field. Negatively charged DNA migrates towards a positive electrode at a rate dependent on their total charge, size, and shape. Most often, DNA is electrophoresed in agarose or polyacrylamide gels. For maximal resolution, polyacrylamide is preferred and for maximal linearity, a denaturant, such as urea is present. A typical gel setup uses a 19:1 mixture of acrylamide:bisacrylamide and a Tris-borate buffer. DNA samples are denatured and applied to the gel, which is usually sandwiched between glass plates. A typical procedure can be found in Sambrook et al. (*Molecular Cloning: A Laboratory Approach*, Cold Spring Harbor Press, NY, 1989) or Ausubel et al. (*Current Protocols in Molecular Biology*, Greene Publishing Co., NY, 1995). Variations may be substituted as long as sufficient resolution is obtained.

Capillary electrophoresis (CE) in its various manifestations (free solution, isotachophoresis, isoelectric focusing, polyacrylamide gel, micellar electrokinetic "chromatography") allows high resolution separations of very small sample volumes. Briefly, in capillary electrophoresis, a neutral coated capillary, such as a 50 μm×37 cm column (eCAP neutral, Beckman Instruments, Calif.), is filled with a linear polyacrylamide (e.g., 0.2% polyacrylamide), a sample is introduced by high-pressure injection followed by an injection of running buffer (e.g., 1×TBE). The sample is electrophoresed and fragments are detected. An order of magnitude increase can be achieved with the use of capillary electrophoresis. Capillaries may be used in parallel for increased throughput (Smith et al., *Nuc. Acids. Res.* 18:4417, 1990; Mathies and Huang, *Nature* 359:167, 1992). Because of the small sample volume that can be loaded onto a capillary, sample may be concentrated to increase level of detection. One means of concentration is sample stacking (Chien and Burgi, *Anal. Chem.* 64:489A, 1992). In sample stacking, a large volume of sample in a low concentration buffer is introduced to the capillary column. The capillary is then filled with a buffer of the same composition, but at higher concentration, such that when the sample ions reach the capillary buffer with a lower electric field, they stack into a concentrated zone. Sample stacking can increase detection by one to three orders of magnitude. Other methods of concentration, such as isotachophoresis, may also be used.

High-performance liquid chromatography (HPLC) is a chromatographic separations technique that separates compounds in solution. HPLC instruments consist of a reservoir of mobile phase, a pump, an injector, a separation column, and a detector. Compounds are separated by injecting an aliquot of the sample mixture onto the column. The different components in the mixture pass through the column at different rates due to differences in their partitioning behavior between the mobile liquid phase and the stationary phase. IP-RO-HPLC on non-porous PS/DVB particles with chemically bonded alkyl chains can also be used to analyze nucleic acid molecules on the basis of size (Huber et al, *Anal. Biochem.* 212:351, 1993; Huber et al., 1993, *Nuc. Acids Res.* 21:1061; Huber et al., *Biotechniques* 16:898, 1993).

In each of these analysis techniques, the amplified fragments are detected. A variety of labels can be used to assist in detection. Such labels include, but are not limited to, radioactive molecules (e.g., $^{35}S$, $^{32}P$, $^{33}P$), fluorescent molecules, and mass spectrometric tags. The labels may be attached to the oligonucleotide primers or to nucleotides that are incorporated during DNA synthesis, including amplification.

Radioactive nucleotides may be obtained from commercial sources; radioactive primers may be readily generated by transfer of label from $\gamma$-$^{32}$P-ATP to a 5'-OH group by a kinase (e.g., T4 polynucleotide kinase). Detection systems include autoradiography, phosphor image analysis and the like.

Fluorescent nucleotides may be obtained from commercial sources (e.g., ABI, Foster City, Calif.) or generated by chemical reaction using appropriately derivatized dyes. Oligonucleotide primers can be labeled, for example, using succinimidyl esters to conjugate to amine-modified oligonucleotides. A variety of fluorescent dyes may be used, including 6-carboxyfluorescein (FAM), 4.7 2'7' tetrachloro 6-carboxyfluorecin (tet), 4.7 2'4'5'7' hexachloro 6-carboxyfluorecin(hex), N', N', N', N' tetramethyl 6-carboxyrhodamine (TAMRA), other carboxyfluorescein derivatives and carboxyrhodamine derivatives, Texas red derivatives, and the like. Chemiluminescent labels (e.g., 1,2-dioxetanes) may also be used. Detection systems include photomultiplier tubes with appropriate wave-length filters for the dyes used.

DNA sequence analysis systems, such as produced by ABI (Foster City, Calif.), may be used.

Labels for detection by mass spectrometry (MS) include releasable tags (see U.S. Pat. Nos. 5,602,273; 5,604,104; 5,610,020), isotopes of sulfur (see U.S. Pat. Nos. 5,003,059; 5,174,962), and mass-differentiating groups (see U.S. Pat. Nos. 5,605,798; 5,547,835; PCT application PCT/US94/00193). Various mass spectrometric techniques are then used to detect the fragments. For example, electrospray ionization MS and matrix-assisted laser-desorption ionization time-of-flight (MALDI) MS are two MS techniques that may be used.

B. Cloning

As noted above, in one aspect of the present invention, the amplified fragments are cloned and may be subsequently subjected to further analysis, such as DNA sequence determination. Although not necessary, the amplification primers may contain sequence recognized by a restriction enzyme. The restriction sites in the primers are generally chosen to allow insertion into a desired vector. As many vectors commonly used have a multiple cloning site (see, for example, New England Biolabs catalogue), the choices of restriction sites are myriad. Within the context of the present invention, the restriction sites are preferably different than those used to digest the cDNAs. Following amplification, the fragments are cleaved with a sequence-specific cleaving agent, if one or more sites are present in the primer sequences, and ligated into a prepared vector. The vector is digested to have compatible ends for ligation of the inserts (i.e., fragments). Ligated vector is transfected into host cells and may be plated for isolation of individual clones.

A wide variety of vectors are available for cloning such amplified fragments. Typically, the vectors will be prokaryotic, such as bacteriophage based vectors, plasmid based vectors, phagemid vectors, and the like. Other organismal vectors may also be used, such as yeast vectors, insect cell vectors, and mammalian vectors. Vectors are readily obtainable, often from commercial sources (e.g., New England Biolabs, MA; Pharmacia, Sweden; Invitrogen, CA) and include pBluescript®, pBC phagemid, pCR-Script™, λgt1, λgt10, λZAP and the like. Procedures and methods for using these vectors and obtaining single, purified clones are well known in the art. Single clones may be subjected to further analysis, such as DNA sequence determination, restriction mapping, hybridization analysis, heteroduplex analysis, and the like.

C. Hybridization to Oligonucleotides

An additional means of analysis is hybridization of the amplified fragments to one or more sets of oligonucleotides immobilized on a solid substrate. Historically, the solid substrate is a membrane, such as nitrocellulose or nylon. More recently, the substrate is a silicon wafer or a borosilicate slide. The substrate may be porous (PCT/US94/12282) or solid. Oligonucleotides are synthesized in situ (see, e.g., U.S. Pat. No. 5,405,783; U.S. Pat. No. 5,412,087; U.S. Pat. No. 5,424,186; U.S. Pat. No. 5,436,327; U.S. Pat. No. 5,429,807; U.S. Pat. No. 5,510,270) or synthesized prior to deposition on the substrate. Various chemistries are known for attaching oligonucleotides (see, e.g, WO 95/35505; U.S. Pat. No. 5,474,796). Many of these attachment chemistries rely upon functionalized oligonucleotides that contain a primary amine group. The oligonucleotides are arranged in an array form, such that the position of each oligonucleotide sequence can be determined.

The amplified fragments, which are generally labeled according to one of the methods described herein, are denatured and applied to the oligonucleotides on the substrate under appropriate salt and temperature conditions. In certain embodiments, the conditions are chosen to favor hybridization of exact complementary matches and disfavor hybridization of mismatched sequences. Unhybridized nucleic acids are washed off and the hybridized molecules detected, generally both for position and quantity. The detection method will depend upon the label used. Radioactive labels, fluorescent labels and mass spectrometry labels are among the suitable labels.

III. USES

As discussed above, molecular identification of gene expression patterns have been the subject of intense endeavor, since the first differentially expressed genes, *S. cerevisiae* galactose genes, were isolated by differential hybridization (St. John and Davis, *Cell* 16: 443, 1979). The recognition that differential gene expression drives biological processes has spurred further development of methodology for identifying and isolating those genes.

Thus, the present invention provides methods and compositions for displaying, identifying, isolating and analyzing genes expressed in cells. These methods may be used to establish signature patterns or profiles of cells that are amenable for comparative analysis with other profiles. These patterns allow comparisons to be made between normal and diseased cells, cells from different organs, cells from the same lineage but at different maturation states, cells untreated or treated to various stimuli, and the like.

Such comparisons may be used to identify the type of cell, determine the origin of cells, identify differentially expressed genes, quantitate expression levels of particular genes; identify agents that activate or inhibit expression of specific genes; identify expressed genes as disease markers; stage tumors; monitor changes in gene expression due to drug action; identify side effects or toxicity; identify disease-specific targets, and monitor treatment and therapies. Moreover, quantitative and qualitative temporal changes can be identified and documented.

Thus, profiles from a variety of normal individuals and cells are collected. Profiles of smooth muscle cells, hematopoietic stem cells, kidney cells, liver cells, skin cells, heart muscle cells, brain cells, peripheral nervous cells, lymphocytes, dendritic cells, lung cells, uterine cells, prostate cells, breast cells, and the like are determined. Similarly, profiles of transformed and diseased cells at different stages are collected. Diseased and normal counterpart cells from the same patient may be used to prepare profiles. Such profiles form a bank of information that can be accessed, preferably in a computerized format, which can be readily retrieved and manipulated.

The present invention may also be used to identify individuals at risk for a specific disease as well as track disease progression. Thus, for example, gene expression profiles for a disease at different stages are generated along with data of treatments and outcome. In this manner, a particular profile may be correlated with an outcome. In such a scheme, a new patient would have a biopsy and expression profile determination. The profile is then compared to the "bank" of profiles, either manually or in a computerized fashion, and, in this way, the disease may be staged and a treatment protocol established. Such comparison profiling may allow predictions of an individual's response to specific drugs. As well, during treatment, the disease can be monitored for a return to a normal state.

Furthermore, individual signals in the patterns may be isolated by conventional cloning techniques, identified, the sequence determined, and the like. Isolated gene sequences are useful for preparation of protein products necessary for drug development, production of antibodies, vaccines, and the like.

Identification of genes associated with the development and progression of cancer or other disorders may be used to facilitate discovery of drugs and diagnostic products to improve treatment and clinical management. For example, an expression profile of a patient's diseased cells and its comparison to expression profiles of patients with known historical outcomes may improve a physician's ability to choose efficacious treatment. These expression profiles may be used to follow treatment, for example, observing whether a patient's pattern shifts toward that of a normal counterpart cell. Profiles may also be used to identify a target gene for drug discovery. By comparing normal cell profiles with diseased cell profiles, genes whose expression is correlated with a disease may be identified. The genes may be isolated and either expression profiles or the gene product used to test potential drugs.

Cancers amenable to the methods described herein include, but are not limited to prostate cancer, breast cancer, glioma, hepatoma, melanoma, other skin cancers, lung cancer, stomach cancer, colorectal cancer, uterine cancer, ovarian cancer, leukemias, bladder cancer, and the like. Other disorders and diseases include osteoporosis; central nervous system diseases (e.g., bipolar disorder, unipolar affective disorder or depression, schizophrenia), Alzheimer's disease, diabetes, heart failure, inflammation, renal diseases, restenosis and other smooth muscle cell diseases, hematopoietic stem cells disorders, and the like.

In addition, the present invention provides the compositions and reagents necessary to practice the invention. An exemplary kit comprises one or more oligonucleotide primers for cDNA synthesis; one or more adapter molecules; and one or more amplification primers. In addition, a kit may contain buffers, cofactors, enzymes, and the like.

The following examples are offered by way of illustration, and not by way of limitation.

EXAMPLES

Example 1

PREPARATION OF RNA FROM ACTIVATED AND NON-ACTIVATED JURKAT CELLS

Jurkat cells, a human T cell line, are grown in RPMI 1640 medium containing 10% (v/v) fetal bovine serum. For some experiments, activated Jurkat cells are used. For activation, cells are serum-starved in RPMI 1640 medium for 24 hours and replenished with 10% fetal bovine serum at a density of $0.2 \times 10^6$ cells per ml and either 50 ng of PMA (phorbol 12-myristate 13-acetate) or 2 µg of PHA (phytohemagglutinin) alone or in combination are added per ml of cell culture for 4 hours. Briefly, RNA is extracted from cells using Trizol reagent (GIBCO/BRL).

Example 2

PREPARATION OF cDNA

Synthesis of cDNA is performed according to standard conditions. A first strand synthesis is set up, without enzyme, using 10 µg total RNA and 2 pmols each of the following primers:

TABLE 1

| Sequence | SEQ ID No. |
|---|---|
| TGAAGCCGAGACGTCGGTCGT$_{18}$A | 1 |
| CAGGGTAGACGACGCTACGCT$_{18}$C | 2 |
| TGGTGGATGGCGTTCCAGGGT$_{18}$G | 3 |

The reaction mixture is layered with mineral oil, incubated at 65° C. for 7 minutes followed by 45° C. for another 7 minutes. Two µl of Superscript reverse transcriptase (200 U/µl, GIBCO/BRL) is added. Synthesis proceeds for 1 hr at 45° C. Second strand synthesis is performed at 16° C. for 2 hours. Following, the cDNAs are precipitated with ethanol and the yield (approximately 100 ng) of cDNA may be determined by conventional methods.

The cDNAs are then digested with restriction enzymes. Typically, a total of 32 enzymes are used. For most analyses, a total of 24 six-cutter restriction enzymes are used.

Example 3

LIGATION OF ADAPTER TO CLEAVED cDNA

The two strands of an adapter are separately synthesized and subsequently annealed. If the adapter is labeled, either label is incorporated into synthesis or after synthesis but before annealing.

The adapter used in this example has the following sequences:

A1: TAGCGTCCGGCGCAGCGACGGCCAG (SEQ No. 4);

A2: GATCCTGGCCGTCGGCTGTCTGTCGGCGC (SEQ. No. 5).

The strands are annealed at a concentration of 50 ng/µl each in 0.1 M NaCl, 10 mM Tris pH 8.0, and 10 mM EDTA. This mixture is heated at 65° C. for 10 minutes, followed by slow cooling to room temperature over approximately 30 minutes. The resulting annealed adapter is partially double stranded and is visualized as a Y-shape.

gatcctggccgtcggctgtctgtcggcgc
gaccggcagcgacgcggcctgcga

Approximately 20 ng of the cDNA is digested with 1.5 units of Bgl II in a 10 µl volume at 37° C. for 1 hr. Two aliquots of 5 µl each of the digested cDNA are ligated to 100 ng (~50 fold excess) of the Y-shaped adapter for 16 hrs at 15° C. Following ligation, one of the reaction mixtures is diluted to 60 µl and heated at 65° C. for 10 minutes to inactivate the T$_4$ DNA ligase. This reaction mix is then processed as described (U.S. application Ser. No. 08/510, 032 and Prashar and Weissman, *Proc. Natl. Acad. Sci. USA* 93:659–663, 1996).

Example 4

AMPLIFICATION OF ADAPTER LIGATED cDNA

The ligated fragments are amplified with a primer whose sequence comprises at least a portion of the sequence of the oligonucleotide primers in the table above and a second primer whose sequence comprises at least a portion of the sequence of one strand of the adapter in the non-complementary portion.

Approximately 100 pg of ligated fragments are amplified using the primers listed in Table 2 as one primer and TAGCGTCCGGCGCAGCGAC (SEQ ID No. 6) as the other primer.

TABLE 2

| Oligonucleotide | SEQ ID No. |
|---|---|
| TGAAGCCGAGACGTCGGTCG(T)$_{18}$AA | 7 |
| TGAAGCCGAGACGTCGGTCG(T)$_{18}$AC | 8 |
| TGAAGCCGAGACGTCGGTCG(T)$_{18}$AG | 9 |
| TGAAGCCGAGACGTCGGTCG(T)$_{18}$AT | 10 |
| CAGGGTAGACGACGCTACGC(T)$_{18}$CA | 11 |
| CAGGGTAGACGACGCTACGC(T)$_{18}$CC | 12 |
| CAGGGTAGACGACGCTACGC(T)$_{18}$CG | 13 |
| CAGGGTAGACGACGCTACGC(T)$_{18}$CT | 14 |
| TGGTGGATGGCGTTCCAGGG(T)$_{18}$GA | 15 |
| TGGTGGATGGCGTTCCAGGG(T)$_{18}$GC | 16 |
| TGGTGGATGGCGTTCCAGGG(T)$_{18}$GG | 17 |
| TGGTGGATGGCGTTCCAGGG(T)$_{18}$GT | 18 |

Amplified products may optionally be detected by 5'-end labeling with $\gamma$-$^{32}$P-ATP using T4 polynucleotide kinase.

The amplification reaction contains approximately 100 pg of fragments, 200 nM primer(s), 200 $\mu$M dNTPs, 20 U of Taq DNA polymerase in 10 mM Tris pH 8, 50 mM KCl and 1.5 mM $MgCl_2$. Primers and dNTPs are added after preheating the reaction mixture containing the remainder of the components to 85° C. This "hot start" avoids artifactual amplification arising from arbitrary annealing of the primers at the lower temperatures occurring during a traditional first cycle (room temperature to 94° C.). The cycle conditions are: 28 to 30 cycles of 94° C. for 30 sec, 56° C. for 2 min, and 72° C. for 30 sec. The reaction is stopped by transferring the tubes to ice. The amplified fragments are extracted once with phenol and once with chloroform. Glycogen is added, and the fragments are precipitated with 7.5 M ammonium acetate and ethanol. The DNA pellet is washed with 70% ethanol and dried.

Following amplification, the products are electrophoresed on a 6% polyacrylamide gel and the amount of fluorescence is determined for each fragment. The even numbered lanes represent the expression profile from activated Jurkat cells and odd number lanes represent the profile from control Jurkat cells.

Bands are extracted from the gels and may be directly cloned or amplified again and cloned into a plasmid, such as pCRscript.

Example 5

RESOLUTION OF AMPLIFICATION OF 3' END FRAGMENTS OF ADAPTER LIGATED cDNA

In this experiment, 3' end fragments of cDNA synthesized from activated and resting Jurkat cells are amplified. Briefly, in this method, double-stranded cDNA, made by the procedure described above, is cleaved with a restriction enzyme and ligated with a partially-double stranded adapter. The 3' end fragments are amplified using a first primer having sequence from the non-complementary region of the adapter and a second primer having sequence from the 5' region of the oligonucleotide primer used in first strand cDNA synthesis.

Figures 2A, 2B:
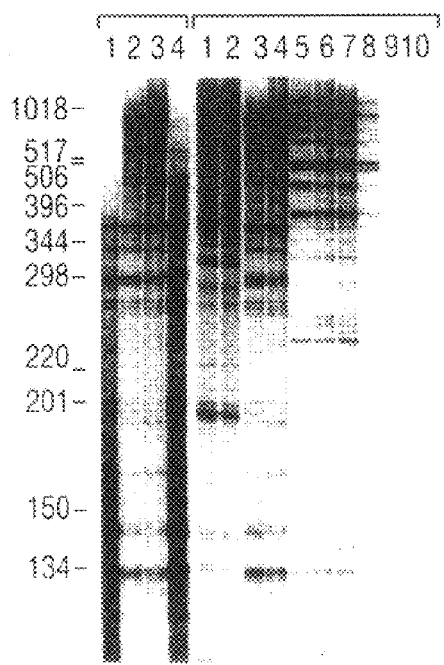
FIGS. 2A–C is a photograph of expression patterns of activated (A, lanes 3 and 4; B, even numbered lanes; C, even numbered lanes) and resting (A, lanes 1 and 2; B, odd numbered lanes; C, odd numbered lanes) Jurkat cells.

Demonstration of reproducibility is shown in FIG. 2, in which panel A, lanes 1 and 2 are replicate amplifications of cDNA from resting Jurkat cells, and lanes 3 and 4 are replicate amplification of cDNA from activated Jurkat cells.

Different fragments are amplified when cDNAs are synthesized using primers with different non-polyA nucleotides, even when the restriction enzyme digestion utilizes the same enzyme. In FIG. 2, panel B, fragments in lanes 1 (odd numbered lanes used RNA from resting Jurkat cells, even-numbered lanes used RNA from activated Jurkat cells) and 2 are generated using a primer with two particular non-polyA nucleotides (RP9.2); fragments in lanes 3 and 4 are generated using a primer with two different non-polyA nucleotides (RP6.0). Different fragments are also amplified when cDNAs are synthesized using the same oligonucleotide primers, but different restriction enzymes (compare FIG. 2, panel B, lanes 5 and 7; lanes 6 and 8).

Lanes 9 and 10 are control lanes in which cDNA is cut with a restriction enzyme but no adapter is ligated. As expected, no amplification is observed in these lanes.

Figure 2C:
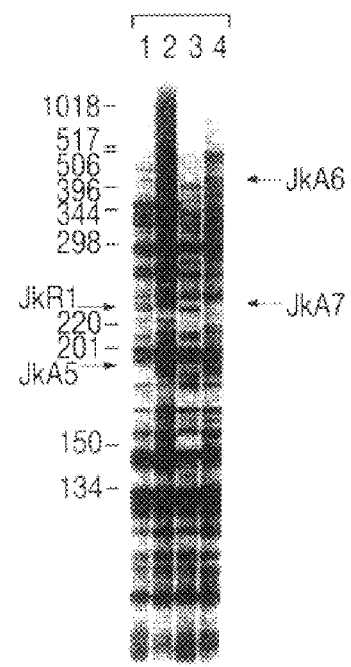

In FIG. 2C, fragments having the same length but different sequences are resolved by digesting the reaction mixture prior to amplification, but after ligation to the adapter. The enzyme is unlikely to cut two co-migrating fragments; the fragment that is digested will not amplify because it lacks an adapter. Specifically, in panel C, the fragments in lanes 1 and 2 are generated according to the method described above; fragments in lanes 3 and 4 are cut with Hinf I prior to amplification. As seen in FIG. 2C, JkA6 and JkA7 are observed as differentially expressed only when the adapter-ligated cDNA is digested with Hinf I prior to amplification.

Using this method, mRNAs that are up- or down-regulated can be observed. For example, the fragments identified as JkA5 in FIG. 2C is present in all lanes indicating that the gene is expressed in both active and resting Jurkat cells. In contrast, the fragment identified as JkA6 is present in lane 4 but not lane 3 indicating that this gene is expressed in activated, but not resting, Jurkat cells. As such, this fragment provides a signature of an activated cell. Furthermore, the fragment identified as JkA7 is expressed in resting cells (lanes 1 and 3), but not in activated cells, providing a signature profile or pattern for resting cells.

Figure 3:
FIG. 3 is a photograph amplification of the 3' ends of 15 different differentially expressed RNAs. The lane on the left is amplification of resting Jurkat cell RNA; the lane on the right used activated Jurkat cell RNA.
Figure 3:
Figure 3:
Figure 3:
Figure 3:
Figure 3:
Figure 3:
Figure 3:
Figure 3:
Figure 3:
Figure 3:
Figure 3:
Figure 3:
Figure 3:
Figure 3:
Figure 3:

The differences in intensity of fragments on the gels correlate to differences in mRNA levels. For example, a total of 15 fragments are isolated, cloned, subjected to DNA sequence analysis and RT-PCR amplification. Of these 15 fragments, by amplification, 14 show changes in levels of expression predicted from the gel pattern (FIG. 3, in which the left lane represents RNA from resting cells, and the right lane represents RNA from active cells; in panel 7, RNA is isolated from peripheral blood T cells). Of the 14 sequences, two are identified as c-myc and IL-2. The remainder are sequences not represented in publicly available sequence databases. In addition, each cloned fragment contains a polyadenylation signal sequence and the expected four base overhang of the adapter, adjacent to the base predicted from the enzyme used for digestion of the duplex cDNA. In every instance, the fragments lack internal cleavage sites for the restriction enzymes used for primary or secondary cutting.

Briefly, RT-PCR is performed by reverse transcribing 1 $\mu$g of total RNA using 100 ng of random hexamer primer in a total volume of 20 $\mu$l. Following heat inactivation of reverse transcriptase, the volume is adjusted to 50 $\mu$l with water, and 2 $\mu$l is amplified in a reaction mixture containing 5 $\mu$l of 10×PCR buffer (10=100 mM Tris, HCl; 500 mM KCl; 15 mM $MgCl_2$), 200 nM of each amplification primer, 200 $\mu$M dNTPs, 1 unit of Amplitaq. The cycle conditions are 30 cycles of 94° C. for 30 sec; 55° C. for 1 min; and 72° C. for 30 sec. The samples are electrophoresed on a 1.5% agarose gel and stained with ethidium bromide.

Example 6

AMPLIFICATION OF 3' END FRAGMENTS OF LOW AMOUNTS OF cDNA

Figure 4:
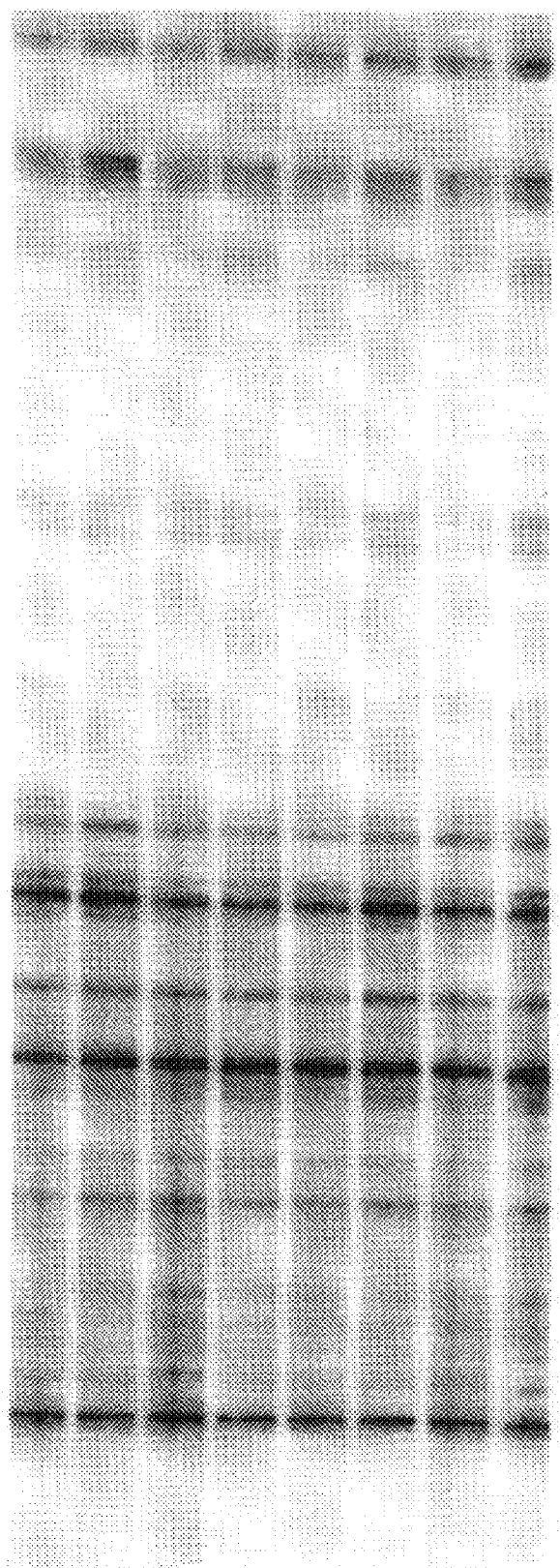
FIG. 4 is a photograph of expression patterns using a low amount of RNA. Lanes 1 and 2, normal amount of RNA; lanes 3 and 4, 25% of duplex cDNA; lanes 5 and 6, 25% of digested duplex cDNA; lanes 7 and 8, 25% ligated fragments.

In this example, low amounts of starting cDNA are used in amplification of 3' end fragments. The data depicted in FIG. 4 shows that 10 $\mu$g of total RNA can be used in conjunction with 30 restriction enzymes to generate a profile of 3' fragments. As shown in FIG. 4, lanes 1 and 2 are generated using normal amount of cDNA, lanes 3 and 4 are generated using 25% of the starting material; lanes 5 and 6 are generated using 25% of digested duplex cDNA; lanes 7 and 8 are generated using 25% of ligated fragments. The results demonstrate that low amounts of cDNA may be used.

Figure 5:
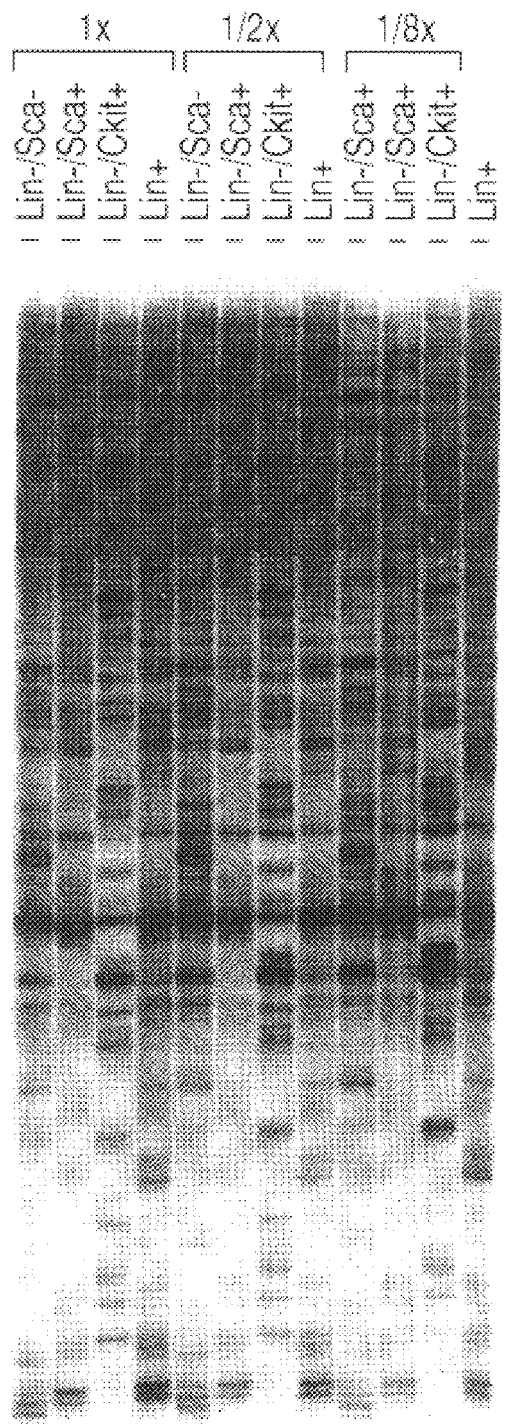
FIG. 5 is a photograph of expression patterns obtained from a small number of murine stem cells and mature cells (Lin+).

In FIG. 5, an expression pattern of 3' fragments of cDNA is generated from a small number of sample cells. More specifically, expression pattern of stem cells at different stages of maturation are compared. For determining the expression profile, total RNA is extracted from 5000 murine stem cells, and used as a template for cDNA synthesis primed from oligo-dT. Double-stranded cDNA is ligated to an adapter, and amplified using oligo-dT and adapter sequence. Thus, the cDNA is amplified prior to further manipulation as described herein. Briefly, an aliquot of this cDNA is incubated with the oligonucleotide primer of step (a). The 3'-end region of the parent cDNA that is single stranded (mainly the polyA region) is removed by a 5'-3' exonuclease activity of DNA polymerase (e.g., T4 DNA polymerase). Following this reaction, dNTPs are added and cDNA is synthesized using a DNA polymerase (e.g., T4 DNA polymerase; E. coli DNA pol I). The duplex cDNA is then subjected to the rest of the protocol of the present invention.

Example 7

DIFFERENTIAL EXPRESSION OF mRNAs

Figure 6:
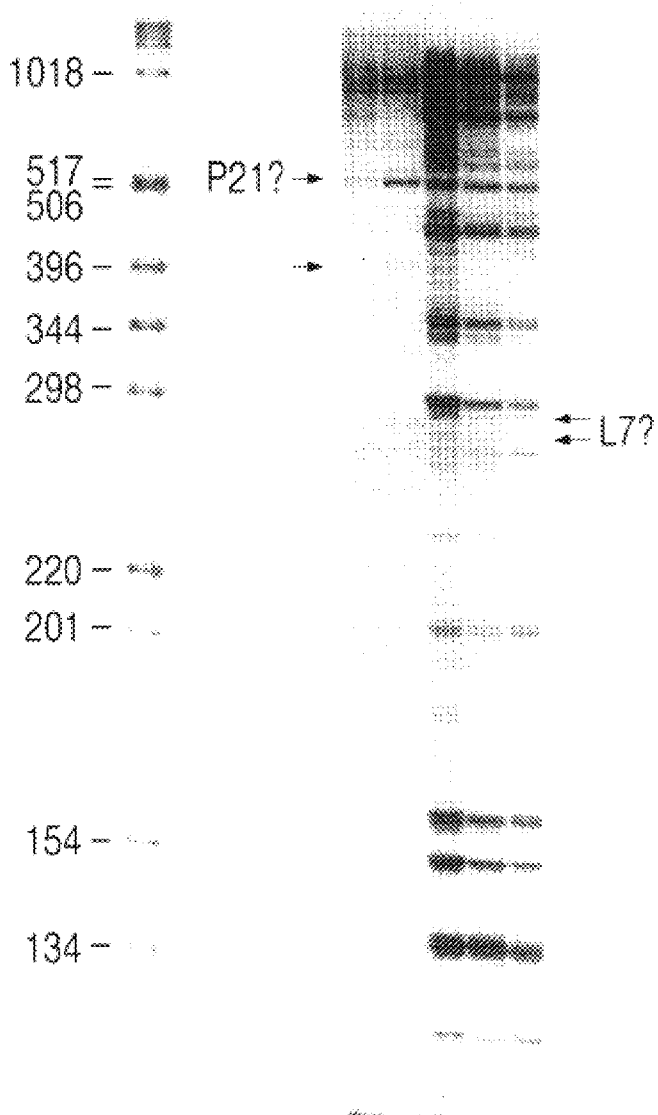
FIG. 6 is a photograph of expression patterns from IMR 90 cells at passages 7, 13, and 22.
Figure 8:
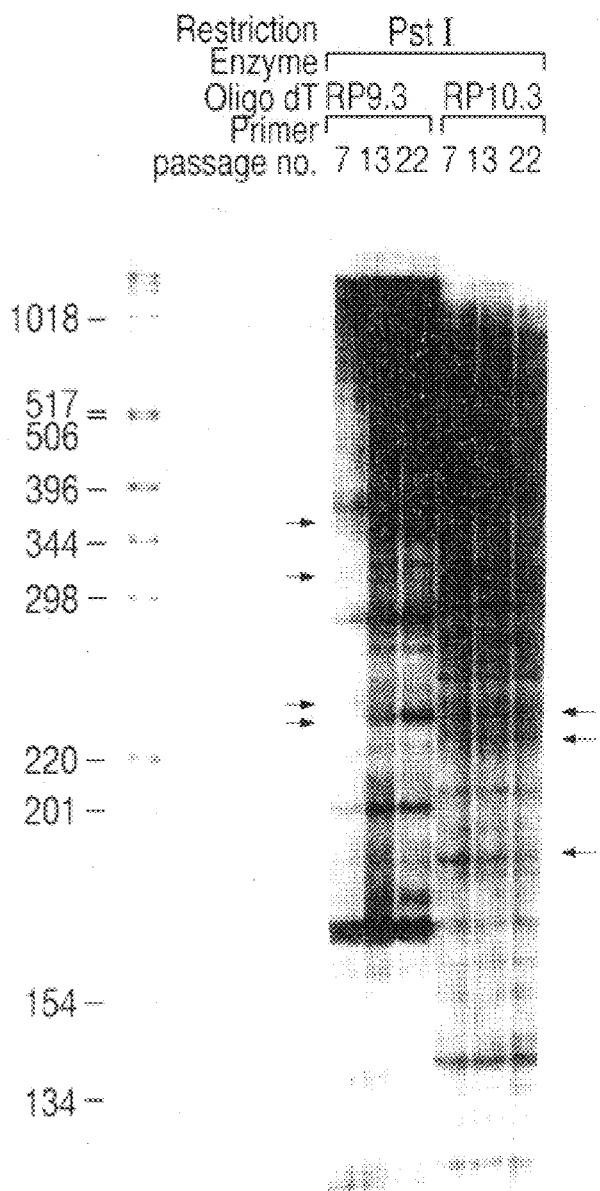
FIG. 8 is a photograph of expression patterns from IMR 90 cells at passages 7, 13, and 22.

By amplification of 3' end fragments of mRNA, expression patterns or profiles are generated and differentially expressed mRNAs are observed. For example, FIG. 6 presents changes that occur in gene expression of aging human IMR 90 fibroblast cell line. For determining gene expression, RNA is isolated from IMR 90 cells at passages 7, 13 and 22. The arrows in FIG. 6 show the position of the 3'-end Bgl II fragment of P21 and L7 genes whose expression changes during aging. The expression patterns of aging IMR 90 are also shown in FIG. 8, in which a different restriction enzyme is used to digest duplex cDNA. The arrows show the position of fragments whose levels change during aging.

Figure 7:
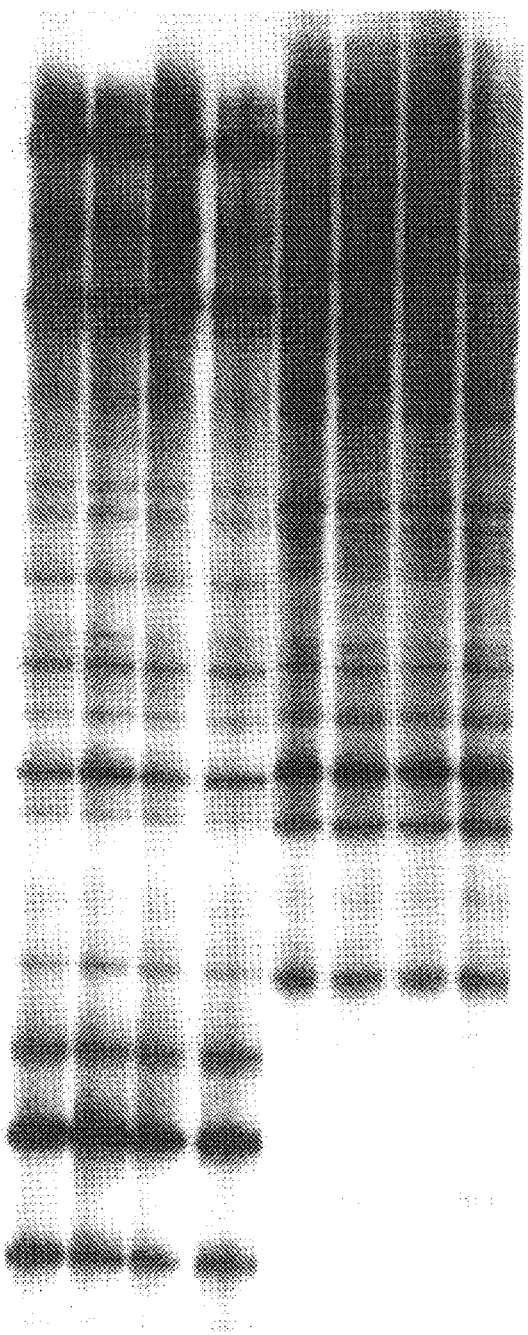
FIG. 7 is a photograph of expression patterns from human osteoblasts untreated (−) or treated (+) with estrogen.

Gene expression also changes in cells exposed to exogenous molecules, such as the hormone estrogen. In FIG. 7, osteoblasts from a 17 year old female patient are obtained from spinal bone chips by allowing cells to grow out of the chips onto plastic culture dishes. The cells are passaged twice and allowed to grow to confluence. After 48 hours of culture in the absence of estrogen, 10 nM 17-β-estradiol is added to the cell culture. Control cells remain in estrogen-free media for 24 hrs. 3' end fragments are amplified from control cell RNA(−) or estrogen treated cell RNA(+). The arrow indicates a fragment present in estrogen treated cells and absent in control cells. Thus, effects of exogenous molecules on various cell types may be determined.

Figure 9:
FIG. 9 is a photograph showing the gene expression patterns of Jurkat cells following transfection with a HOX11 gene. Lane 1, 1 kb marker; lane 2, Jurkat cells transfected with the control vector ptet-tak; lane 3, Jurkat cells transfected with the control vector ptet-splice; lane 4, Jurkat T cells transfected with the control vector ptet-HOX11; lane 5, Jurkat cells transfected with the vectors ptet-tak + ptet-HOX11, taken at 0 hours after transfection; and lane 6, Jurkat cells transfected with the vectors ptet-tak and ptet-HOX11 taken 1 hour after transfection.

The expression pattern of Jurkat cell RNA after transfection with the 30 HOX11 gene is shown in FIG. 9. Overexpression of the HOX11 gene in T cells is implicated in leukemia (Hatano et al., *Blood* (Suppl.) 80: 355a, 1992). In order to determine which RNAs are induced as a result of HOX11 overexpression, the cDNA for HOX11 is transfected into Jurkat cells according to a standard protocol using a tet expression vector (Shockett et al., *Proc. Natl. Acad. Sci. USA* 92:6522, 1995). The cDNA expression patterns between non-transfected and HOX11 transfected Jurkat cells are then compared. As depicted in FIG. 9, the arrows indicate some of the fragments induced as a result of HOX11 cDNA overexpression.

It will be appreciated that, although specific embodiments of the invention have been described herein for purposes of illustration, various modifications may be made without departing from the spirit and scope of the invention. Accordingly, the invention is not limited except as by the appended claims.

We claim:

1. A method for selectively amplifying in a nucleic acid sample DNA fragments having sequences corresponding to 3' ends of mRNAs, comprising the steps of:

(a) contacting the mRNAs with oligonucleotide primers comprising a 5' sequence incapable of hybridizing to a polyA tail of the mRNAs, and a 3' sequence that hybridizes to a portion of the polyA tail of the mRNAs and n non-polyA nucleotides immediately upstream of the polyA tail, wherein n is at least one;

(b) reverse transcribing the mRNA to produce a first strand cDNA complementary to the mRNA that includes the oligonucleotide primer;

(c) synthesizing a second DNA strand complementary to the first strand cDNA to form a duplex;

(d) cleaving the duplex with at least one sequence-specific cleaving agent to provide a number of duplex cleavage fragments;

(e) ligating an adapter to the cleavage fragments, the adapter consisting of two partially hybridized nucleic acid strands, wherein portions of the two strands are non-complementary to each other and portions of the two strands are complementary to each other; and (f) amplifying the ligated cleaved fragments of step (e) using a set of primers, in which for each set the first primer comprises the 5' sequence incapable of hybridizing to a polyA tail of the mRNAs, and the 3' sequence that hybridizes to a portion of the polyA tail of the mRNAs and at least n+1 non-polyA nucleotides immediately upstream of the polyA tail, and a second primer whose sequence comprises at least a portion of the sequence of one strand of the adapter in the non-complementary portion, thereby selectively amplifying a DNA fragment comprising sequence complementary to an 3' region of an mRNA.

2. The method of claim 1, wherein each oligonucleotide primer in step (a) has a different 5' sequence.

3. The method of claim 1, wherein the contacting step is performed with a mixture of oligonucleotide primers.

4. The method of claim 1, wherein the oligonucleotide primer of step (a) has one non-polyA nucleotide and the first primer of step (f) has two non-polyA nucleotides.

5. The method of claim 4, wherein the oligonucleotide primer is a mixture of 3 primers having 5'-A-3', 5'-C-3', 5'-G-3' as the non-polyA hybridizing nucleotide and the first primer of step (f) is a mixture of 12 primers having 5'-AA-3', 5'-AT-3', 5'-AC-3', 5'-AG-3', 5'-CA-3', 5'-CT-3', 5'-CC-3', 5'-CG-3', 5'-GA-3', 5'-GT-3', 5'-GC-3', and 5'-GG-3' as the non-polyA hybridizing nucleotides.

6. The method of claim 1, wherein each set of primers in step (f) are used in a separate amplification.

7. The method of claim 1, wherein the 5' sequence of one or both of the primer sequences in step (f) comprises a recognition sequence for a restriction enzyme.

8. The method of claim 1, wherein the adapter comprises a first portion, wherein the two strands are noncomplementary to each other and a second portion, wherein the two strands are complementary to each other, resulting in a partially hybridized adapter that is Y-shaped.

9. The method of claim 8, wherein one of the two strands of the noncomplementary portion comprises a recognition sequence for a restriction enzyme.

10. The method of claim 1, wherein the mRNAs are isolated from cells or tissue.

11. The method of claim 1, wherein at least one of the primers in step (f) is labeled.

12. The method of claim 11, wherein the label is a fluorescent label.

13. The method of claim 1, wherein the cleaving agent is a restriction enzyme.

14. A method for selectively isolating in a nucleic acid sample DNA fragments having sequences corresponding to 3' ends of mRNAs, comprising the steps of:
  (a) contacting the mRNAs with oligonucleotide primers comprising a 5' sequence incapable of hybridizing to a polyA tail of the mRNAs, and a 3' sequence that hybridizes to a portion of the polyA tail of the mRNAs and n non-polyA nucleotides immediately upstream of the polyA tail, wherein n is at least one;
  (b) reverse transcribing the mRNA to produce a first strand cDNA complementary to the mRNA that includes the oligonucleotide primer;
  (c) synthesizing a second DNA strand complementary to the first strand cDNA to form a duplex;
  (d) cleaving the duplex with at least one sequence-specific cleaving agent to provide a number of duplex cleavage fragments;
  (e) ligating an adapter to the cleavage fragments, the adapter consisting of two partially hybridized nucleic acid strands, wherein portions of the two strands are non-complementary to each other and portions of the two strands are complementary to each other;
  (f) amplifying the ligated cleaved fragments of step (e) using a set of primers, in which for each set the first primer comprises the 5' sequence incapable of hybridizing to a polyA tail of the mRNAs, and the 3' sequence that hybridizes to a portion of the polyA tail of the mRNAs and at least n+1 non-polyA nucleotides immediately upstream of the polyA tail, and a second primer whose sequence comprises at least a portion of the sequence of one strand of the adapter in the non-complementary portion, thereby selectively amplifying a DNA fragment comprising sequence complementary to an 3' region of an mRNA; and
  (g) isolating the amplified fragment of step (f).

15. A method for selectively cloning from a nucleic acid sample DNA fragments having sequences corresponding to 3' ends of mRNAs, comprising the steps of:
  (a) contacting the mRNAs with oligonucleotide primers comprising a 5' sequence incapable of hybridizing to a polyA tail of the mRNAs, and a 3' sequence that hybridizes to a portion of the polyA tail of the mRNAs and n non-polyA nucleotides immediately upstream of the polyA tail, wherein n is at least one;
  (b) reverse transcribing the mRNA to produce a first strand cDNA complementary to the mRNA that includes the oligonucleotide primer;
  (c) synthesizing a second DNA strand complementary to the first strand cDNA to form a duplex;
  (d) cleaving the duplex with at least one sequence-specific cleaving agent to provide a number of duplex cleavage fragments;
  (e) ligating an adapter to the cleavage fragments, the adapter consisting of two partially hybridized nucleic acid strands, wherein portions of the two strands are non-complementary to each other and portions of the two strands are complementary to each other;
  (f) amplifying the ligated cleaved fragments of step (e) using a set of primers, in which for each set the first primer comprises the 5' sequence incapable of hybridizing to a polyA tail of the mRNAs, and the 3' sequence that hybridizes to a portion of the polyA tail of the mRNAs and at least n+1 non-polyA nucleotides immediately upstream of the polyA tail, and a second primer whose sequence comprises at least a portion of the sequence of one strand of the adapter in the non-complementary portion, thereby selectively amplifying a DNA fragment comprising sequence complementary to an 3' region of an mRNA; and
  (g) cloning the isolated fragment of step (f).

16. The method of claim 15, wherein the cloning step comprises:
  (g)(1) digesting the amplified fragments in step (f) with a restriction enzyme, and
  (g)(2) ligating the digested fragments of step (g)(1) to a vector.

17. The method of claim 15, further comprising:
  (h) determining the DNA sequence of cloned fragments.

18. A method for analyzing in a nucleic acid sample DNA fragments having sequences corresponding to 3' ends of mRNAs, comprising the steps of:
  (a) contacting the mRNAs with oligonucleotide primers comprising a 5' sequence incapable of hybridizing to a polyA tail of the mRNAs, and a 3' sequence that hybridizes to a portion of the polyA tail of the mRNAs and n non-polyA nucleotides immediately upstream of the polyA tail, wherein n is at least one;
  (b) reverse transcribing the mRNA to produce a first strand cDNA complementary to the mRNA that includes the oligonucleotide primer;
  (c) synthesizing a second DNA strand complementary to the first strand cDNA to form a duplex;
  (d) cleaving the duplex with at least one sequence-specific cleaving agent to provide a number of duplex cleavage fragments;
  (e) ligating an adapter to the cleavage fragments, the adapter consisting of two partially hybridized nucleic acid strands, wherein portions of the two strands are non-complementary to each other and portions of the two strands are complementary to each other;
  (f) amplifying the ligated cleaved fragments of step (e) using a set of primers, in which for each set the first primer comprises the 5' sequence incapable of hybridizing to a polyA tail of the mRNAs, and the 3' sequence that hybridizes to a portion of the polyA tail of the mRNAs and at least n+1 non-polyA nucleotides immediately upstream of the polyA tail, and a second primer whose sequence comprises at least a portion of the sequence of one strand of the adapter in the non-complementary portion, thereby selectively amplifying a DNA fragment comprising sequence complementary to an 3' region of an mRNA; and
  (g) isolating the amplified fragment of step (f); and
  (h) analyzing the isolated fragment of step (g).

19. The method of claim 18, wherein the analyzing step comprises:

(h)(1) determining the DNA sequences of the fragments.

20. The method of claim 18, wherein the analyzing step comprises:

(h)(1) hybridizing the fragments to nucleic acid molecules.

21. A method for selectively detecting in a nucleic acid sample DNA fragments having sequence complementary to 3' ends of mRNAs, comprising the steps of:

(a) contacting the mRNAs with oligonucleotide primers comprising a 5' sequence incapable of hybridizing to a polyA tail of the mRNAs, and a 3' sequence that hybridizes to a portion of the polyA tail of the mRNAs and n non-polyA nucleotides immediately upstream of the polyA tail, wherein n is at least one;

(b) reverse transcribing the mRNA to produce a first strand cDNA complementary to the mRNA that includes the oligonucleotide primer;

(c) synthesizing a second DNA strand complementary to the first strand cDNA to form a duplex;

(d) cleaving the duplex with at least one sequence-specific cleaving agent to provide a number of duplex cleavage fragments;

(e) ligating an adapter to the cleavage fragments, the adapter consisting of two partially hybridized nucleic acid strands, wherein portions of the two strands are non-complementary to each other and portions of the two strands are complementary to each other;

(f) amplifying the ligated cleaved fragments of step (e) using a set of primers, in which for each set the first primer comprises the 5' sequence incapable of hybridizing to a polyA tail of the mRNAs, and the 3' sequence that hybridizes to a portion of the polyA tail of the mRNAs and at least n+1 non-polyA nucleotides immediately upstream of the polyA tail, and a second primer whose sequence comprises at least a portion of the sequence of one strand of the adapter in the non-complementary portion, thereby selectively amplifying a DNA fragment comprising sequence complementary to an 3' region of an mRNA; and (g) detecting the amplified fragments of step (f).

22. The method of claim 21, wherein the detecting step comprises:

hybridizing the fragments to nucleic acid molecules.

23. The method of claim 22, wherein the nucleic acid molecules are attached to a silicon wafer or porous glass wafer.

24. The method of claim 22, wherein the nucleic acid molecules are oligonucleotides from about 25 to about 40 nucleotides long.

25. The method of claim 22, wherein the nucleic acid molecules comprise a set of cDNA sequences.

26. The method of claim 20, wherein the fragments are labeled.

27. A method for comparing the levels of mRNA expression in two cell populations, comprising:

selectively amplifying in a nucleic acid sample from each cell population DNA fragments having sequences corresponding to 3' portions of mRNAs, comprising the steps of:

(a) contacting the mRNAs with oligonucleotide primers comprising a 5' sequence incapable of hybridizing to a polyA tail of the mRNAs, and a 3' sequence that hybridizes to a portion of the polyA tail of the mRNAs and n non-polyA nucleotides immediately upstream of the polyA tail, wherein n is at least one;

(b) reverse transcribing the mRNA to produce a first strand cDNA complementary to the mRNA that includes the oligonucleotide primer;

(c) synthesizing a second DNA strand complementary to the first strand cDNA to form a duplex;

(d) cleaving the duplex with at least one sequence-specific cleaving agent to provide a number of duplex cleavage fragments;

(e) ligating an adapter to the cleavage fragments, the adapter consisting of two partially hybridized nucleic acid strands, wherein portions of the two strands are non-complementary to each other and portions of the two strands are complementary to each other;

(f) amplifying the ligated cleaved fragments of step (e) using a set of primers, in which for each set the first primer comprises the 5' sequence incapable of hybridizing to a polyA tail of the mRNAs, and the 3' sequence that hybridizes to a portion of the polyA tail of the mRNAs and at least n+1 non-polyA nucleotides immediately upstream of the polyA tail, and a second primer whose sequence comprises at least a portion of the sequence of one strand of the adapter in the non-complementary portion, thereby selectively amplifying a DNA fragment comprising sequence complementary to an 3' region of an mRNA; and (g) comparing the amounts of amplified fragments obtained in step (f).

28. The method of claim 27, wherein one of the cell populations is treated.

29. The method of claim 27, wherein one of the cell populations is a tumor cell population.

30. A method for selectively amplifying in a nucleic acid sample DNA fragments having sequences corresponding to 3' ends of mRNAs, comprising the steps of:

(a) contacting the mRNAs with oligonucleotide primers comprising a sequence that hybridizes to a portion of the polyA tail of the mRNAs and n non-polyA nucleotides immediately upstream of the polyA tail, wherein n is at least one;

(b) reverse transcribing the mRNA to produce a first strand cDNA complementary to the mRNA that includes the oligonucleotide primer;

(c) synthesizing a second DNA strand complementary to the first strand cDNA to form a duplex;

(d) cleaving the duplex with at least one sequence-specific cleaving agent to provide a number of duplex cleavage fragments;

(e) ligating an adapter to the cleavage fragments, the adapter consisting of two partially hybridized nucleic acid strands, wherein portions of the two strands are non-complementary to each other and portions of the two strands are complementary to each other;

(f) amplifying the ligated cleaved fragments of step (e) using a set of primers, in which for each set the first primer comprises the sequence that hybridizes to a portion of the polyA tail, of the mRNAs and n+1 non-polyA nucleotides immediately upstream of the polyA tail, and a second primer whose sequence comprises at least a portion of the sequence of one strand of the adapter in the non-complementary portion, thereby selectively amplifying a DNA fragment comprising sequence complementary to an 3' region of an mRNA.

31. A method for selectively amplifying in a nucleic acid sample DNA fragments having sequences corresponding to 3' ends of mRNAs, comprising:

a) synthesizing cDNA with a set of oligonucleotide primers, wherein said set is comprised of primers comprising nucleotides which partially hybridize to the poly A tail of mRNAs and further comprise n non-poly A nucleotides at their 3' ends, wherein n is at least one;

b) cleaving the cDNA of step (a) with at least one sequence specific agent, wherein the resulting cleaved site is ligated to an adaptor; and c) amplifying the product of step (b) using a set of primers, wherein the primer set comprises nucleotide sequences that comprise at least n+1 non-poly A nucleotides at their 3' ends and further comprise sequences complementary to the poly A tail of the mRNAs, and a second primer, wherein the second primer comprises a sequence complementary to a sequence comprised in the adaptor of step (b).

32. A method for selectively amplifying in a nucleic acid sample DNA fragments having sequences corresponding to 3' ends of mRNAs, comprising:

a) synthesizing cDNA with a set of oligonucleotide primers, wherein said set is comprised of primers comprising nucleotides which partially hybridize to the poly A tail of mRNAs and further comprise n non-poly A nucleotides at their 3' ends, wherein n is at least one;

b) cleaving the cDNA of step (a) with at least one sequence specific agent;

c) ligating an adaptor consisting of two partially hybridized nucleic acid strands, wherein portions of the two strands are non-complementary to each other and portions of the two strands are complementary to each other, to the cleaved cDNA of step (b); and d) amplifying the product of step (b) using a set of primers, wherein the primer set comprises nucleotide sequences that comprise at least n+1 non-poly A nucleotides at their 3' ends and further comprise sequences complementary to the poly A tail of the mRNAs, and a second primer, wherein the second primer comprises a sequence complementary to the non-complementary portion of the sequence comprised in the adaptor of step (c).

33. The method of claim 31 or 32, wherein each oligonucleotide primer in step (a) has a different sequence of nucleotides that comprises the 5' end.

34. The method of claim 31 or 32, wherein the oligonucleotide primer of step (a) has one non-polyA nucleotide and the first primer of the amplifying step has two non-polyA nucleotides.

35. The method of claim 34, wherein the oligonucleotide primer is a mixture of 3 primers having 5'-A-3', 5'-C-3', 5'-G-3' as the non-polyA hybridizing nucleotide and the first primer of the amplifying step is a mixture of 12 primers having 5'-AA-3', 5'-AT-3', 5'-AC-3', 5'-AG-3', 5'-CA-3', 5'-CT-3', 5'-CC-3', 5'-CG-3', 5'-GA-3', 5'-GT-3', 5'-GC-3', and 5'-GG-3' as the non-polyA hybridizing nucleotides.

36. The method of claim 31 or 32, wherein each set of primers in the amplifying step is used in a separate amplification.

37. The method of claim 31 or 32, wherein the nucleotide sequence that comprises the 5' end of one or both of the primer sequences in the amplifying step comprises a recognition sequence for a restriction enzyme.

38. The method of claim 31, wherein the adapter of step (b) comprises a first portion, wherein the two strands are non-complementary to each other and a second portion, wherein the two strands are complementary to each other, resulting in a partially hybridized adapter that is Y-shaped.

39. The method of claim 38, wherein one of the two strands of the non-complementary portion of the adaptor comprises a recognition sequence for a restriction enzyme.

40. The method of claim 31 or 32, wherein the nucleic acid sample is mRNA.

41. The method of claim 40, wherein the mRNA is isolated from cells or tissue.

42. The method of claim 31 or 32, wherein at least one of the primers in the amplifying step is labeled.

43. The method of claim 42, wherein the label is a fluorescent label.

44. The method of claim 31 or 32, wherein the cleaving agent is a restriction enzyme.

45. A method for selectively isolating in a nucleic acid sample DNA fragments having sequences corresponding to 3' ends of mRNAs, comprising:

a) synthesizing cDNA with a set of oligonucleotide primers, wherein said set is comprised of primers comprising nucleotides which partially hybridize to the poly A tail of mRNAs and further comprise n non-poly A nucleotides at their 3' ends, wherein n is at least one;

b) cleaving the cDNA of step (a) with at least one sequence specific agent, wherein the resulting cleaved site is ligated to an adaptor; and c) amplifying the product of step (b) using a set of primers, wherein the primer set comprises nucleotide sequences that comprise at least n+1 non-poly A nucleotides at their 3' ends and further comprise sequences complementary to the poly A tail of the mRNAs, and a second primer, wherein the second primer comprises a sequence complementary to a sequence comprised in the adaptor of step (b); and d) isolating the amplified fragments of step (c).

46. A method for selectively cloning in a nucleic acid sample DNA fragments having sequences corresponding to 3' ends of mRNAs, comprising:

a) synthesizing cDNA with a set of oligonucleotide primers, wherein said set is comprised of primers comprising nucleotides which partially hybridize to the poly A tail of mRNAs and further comprise n non-poly A nucleotides at their 3' ends, wherein n is at least one;

b) cleaving the cDNA of step (a) with at least one sequence specific agent, wherein the resulting cleaved site is ligated to an adaptor; and c) amplifying the product of step (b) using a set of primers, wherein the primer set comprises nucleotide sequences that comprise at least n+1 non-poly A nucleotides at their 3' ends and further comprise sequences complementary to the poly A tail of the mRNAs, and a second primer, wherein the second primer comprises a sequence complementary to a sequence comprised in the adaptor of step (b); and d) isolating the amplified fragments of step (c) and cloning the isolated fragments.

47. The method of claim 46, wherein the cloning step comprises:

d)(1) digesting the amplified fragments of step (c) with a restriction enzyme, and d)(2) ligating the digested fragments to a vector.

48. The method of claim 46, further comprising:

e) determining the DNA sequence of cloned fragments.

49. A method for analyzing in a nucleic acid sample DNA fragments having sequences corresponding to 3' ends of mRNAs, comprising:

a) synthesizing cDNA with a set of oligonucleotide primers, wherein said set is comprised of primers comprising nucleotides which partially hybridize to the poly A tail of mRNAs and further comprise n non-poly A nucleotides at their 3' ends, wherein n is at least one;

b) cleaving the cDNA of step (a) with at least one sequence specific agent, wherein the resulting cleaved site is ligated to an adaptor; and c) amplifying the product of step (b) using a set of primers, wherein the primer set comprises nucleotide sequences that comprise at least n+1 non-poly A nucleotides at their 3' ends and further comprise sequences complementary to the poly A tail of the mRNAs, and a second primer, wherein the second primer comprises a sequence complementary to a sequence comprised in the adaptor of step (b);

d) isolating the amplified fragments of step (c); and e) analyzing the isolated fragments of step (d).

50. The method of claim 49, wherein the analyzing step comprises:

(e)(1) determining the DNA sequences of the fragments.

51. The method of claim 49, wherein the analyzing step comprises;

(e)(1) hybridizing the fragments to nucleic acid molecules.

52. A method for selectively detecting in a nucleic acid sample DNA fiagments having sequences corresponding to 3' ends of mRNAs, comprising:

a) synthesizing cDNA with a set of oligonucleotide primers, wherein said set is comprised of primers comprising nucleotides which partially hybridize to the poly A tail of mRNAs and further comprise n non-poly A nucleotides at their 3' ends, wherein n is at least one;

b) cleaving the cDNA of step (a) with at least one sequence specific agent, wherein the resulting cleaved site is ligated to an adaptor; and c) amplifying the product of step (b) using a set of primers, wherein the primer set comprises nucleotide sequences that comprise at least n+1 non-poly A nucleotides at their 3' ends and further comprise sequences complementary to the poly A tail of the mRNAs, and a second primer, wherein the second primer comprises a sequence complementary to a sequence comprised in the adaptor of step (b); and d) detecting the amplified fragments of step (c).

53. The method of claim 52, wherein the detecting step comprises:

(d)(1) hybridizing the fragments to nucleic acid molecules.

54. The method of claim 53, wherein the nucleic acid molecules are attached to a silicon wafer or porous glass wafer.

55. The method of claim 53, wherein the nucleic acid molecules are oligonucleotides from about 25 to about 40 nucleotides long.

56. The method of claim 52, wherein the nucleic acid molecules comprise a set of cDNA sequences.

57. The method of claim 53, wherein the fragments are labeled.

58. A method for comparing the levels of mRNA expression in two cell populations, comprising:

selectively amplifying in a nucleic acid sample from each cell population DNA fragments having sequences corresponding to 3' portions of mRNAs, comprising:

a) synthesizing cDNA with a set of oligonucleotide primers, wherein said set is comprised of primers comprising nucleotides which partially hybridize to the poly A tail of mRNAs and further comprise n non-poly A nucleotides at their 3' ends, wherein n is at least one;

b) cleaving the cDNA of step (a) with at least one sequence specific agent, wherein the resulting cleaved site is ligated to an adaptor; and c) amplifying the product of step (b) using a set of primers, wherein the primer set comprises nucleotide sequences that comprise at least n+1 non-poly A nucleotides at their 3' ends and further comprise sequences complementary to the poly A tail of the mRNA, and wherein the second primer comprises a sequence complementary to a sequence comprised in the adaptor of step (b); and d) comparing the amounts of amplified fragments obtained in step (c) between the two populations.

59. The method of claim 58, wherein one of the cell populations is treated.

60. The method of claim 59, wherein one of the cell populations is a tumor cell population.

61. The method of claim 31, wherein when said set of primers of step (a) comprises n non poly-A nucleotides at their 3' ends and n is at least one, the number of separate primers in said set is $3(4)^{n-1}$.

62. The method of any one of claims 45, 46, 49, 52, or 58, wherein the adapter of step (b) comprises a first portion, wherein the two strands are non-complementary to each other, and a second portion, wherein the two strands are complementary to each other.

63. The method of claim 62, wherein the adapter is Y-shaped.

* * * * *

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 39 base pairs
      (B) TYPE: nucleic acid
      (C) STRANDEDNESS: single
      (D) TOPOLOGY: linear (xi) SEQUENCE DESCRIPTION: SEQ ID NO:1:

TGAAGCCGAG ACGTCGGTCG TTTTTTTTTT TTTTTTTA                    39

(2) INFORMATION FOR SEQ ID NO:2:

(i) SEQUENCE CHARACTERISTICS:
      (A) LENGTH: 39 base pairs
      (B) TYPE: nucleic acid
      (C) STRANDEDNESS: single
      (D) TOPOLOGY: linear (xi) SEQUENCE DESCRIPTION: SEQ ID NO:2:

CAGGGTAGAC GACGCTACGC TTTTTTTTTT TTTTTTTC                    39

(2) INFORMATION FOR SEQ ID NO:3:

(i) SEQUENCE CHARACTERISTICS:
      (A) LENGTH: 39 base pairs (B) TYPE: nucleic acid
        (C) STRANDEDNESS: single
        (D) TOPOLOGY: linear (xi) SEQUENCE DESCRIPTION: SEQ ID NO:3:

TGGTGGATGG CGTTCCAGGG TTTTTTTTTT TTTTTTTTG                               39

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:4:

TAGCGTCCGG CGCAGCGACG GCCAG                                              25

(2) INFORMATION FOR SEQ ID NO:5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:5:

GATCCTGGCC GTCGGCTGTC TGTCGGCGC                                          29

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:6:

TAGCGTCCGG CGCAGCGAC                                                     19

(2) INFORMATION FOR SEQ ID NO:7:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:7:

TGAAGCCGAG ACGTCGGTCG TTTTTTTTTT TTTTTTTTAA                              40

(2) INFORMATION FOR SEQ ID NO:8:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:8:

TGAAGCCGAG ACGTCGGTCG TTTTTTTTTT TTTTTTTAC                               40

(2) INFORMATION FOR SEQ ID NO:9:

(i) SEQUENCE CHARACTERISTICS:
        (A) LENGTH: 40 base pairs
        (B) TYPE: nucleic acid (C) STRANDEDNESS: single
        (D) TOPOLOGY: linear (xi) SEQUENCE DESCRIPTION: SEQ ID NO:9:

TGAAGCCGAG ACGTCGGTCG TTTTTTTTTT TTTTTTTTAG                 40

(2) INFORMATION FOR SEQ ID NO:10:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:10:

TGAAGCCGAG ACGTCGGTCG TTTTTTTTTT TTTTTTTTAT                 40

(2) INFORMATION FOR SEQ ID NO:11:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:11:

CAGGGTAGAC GACGCTACGC TTTTTTTTTT TTTTTTTTCA                 40

(2) INFORMATION FOR SEQ ID NO:12:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:12:

CAGGGTAGAC GACGCTACGC TTTTTTTTTT TTTTTTTTCC                 40

(2) INFORMATION FOR SEQ ID NO:13:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:13:

CAGGGTAGAC GACGCTACGC TTTTTTTTTT TTTTTTTTCG                 40

(2) INFORMATION FOR SEQ ID NO:14:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:14:

CAGGGTAGAC GACGCTACGC TTTTTTTTTT TTTTTTTTCT                 40

(2) INFORMATION FOR SEQ ID NO:15:

(i) SEQUENCE CHARACTERISTICS:
        (A) LENGTH: 40 base pairs
        (B) TYPE: nucleic acid
        (C) STRANDEDNESS: single (D) TOPOLOGY: linear (xi) SEQUENCE DESCRIPTION: SEQ ID NO:15:

TGGTGGATGG CGTTCCAGGG TTTTTTTTTT TTTTTTTTGA        40

(2) INFORMATION FOR SEQ ID NO:16:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:16:

TGGTGGATGG CGTTCCAGGG TTTTTTTTTT TTTTTTTTGC        40

(2) INFORMATION FOR SEQ ID NO:17:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:17:

TGGTGGATGG CGTTCCAGGG TTTTTTTTTT TTTTTTTTGG        40

(2) INFORMATION FOR SEQ ID NO:18:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:18:

TGGTGGATGG CGTTCCAGGG TTTTTTTTTT TTTTTTTTGT        40